(12) United States Patent
Rossing et al.

(10) Patent No.: US 7,835,797 B2
(45) Date of Patent: Nov. 16, 2010

(54) METHOD AND SYSTEM FOR IMPLANTABLE PRESSURE TRANSDUCER FOR REGULATING BLOOD PRESSURE

(75) Inventors: Martin A. Rossing, Coon Rapids, MN (US); Eric Irwin, Minneapolis, MN (US)

(73) Assignee: CVRx, Inc., Minneapolis, MN (US)

( * ) Notice: Subject to any disclaimer, the term of this patent is extended or adjusted under 35 U.S.C. 154(b) by 291 days.

(21) Appl. No.: 11/950,092

(22) Filed: Dec. 4, 2007

(65) Prior Publication Data

US 2009/0143837 A1 Jun. 4, 2009

(51) Int. Cl.
*A61N 1/00* (2006.01)

(52) U.S. Cl. .......................................... 607/44

(58) Field of Classification Search ............... 607/2, 607/3, 9
See application file for complete search history.

(56) References Cited

U.S. PATENT DOCUMENTS

| | | | |
|---|---|---|---|
| 3,996,925 | A | 12/1976 | Djordjevich |
| 4,485,813 | A | 12/1984 | Anderson et al. |
| 4,562,843 | A | 1/1986 | Djordjevich et al. |
| 5,003,976 | A | 4/1991 | Alt |
| 5,063,937 | A | 11/1991 | Ezenwa et al. |
| 6,024,704 | A | 2/2000 | Meador et al. |
| 6,073,048 | A | 6/2000 | Kieval et al. |
| 6,277,078 | B1 | 8/2001 | Porat et al. |
| 6,360,123 | B1 | 3/2002 | Kimchi et al. |
| 6,522,926 | B1 | 2/2003 | Kieval et al. |
| 6,645,143 | B2 | 11/2003 | Van Tassel et al. |
| 6,652,464 | B2 | 11/2003 | Schwartz et al. |
| 7,029,447 | B2 | 4/2006 | Rantala |
| 7,147,604 | B1 | 12/2006 | Allen et al. |
| 2003/0149450 | A1 * | 8/2003 | Mayberg .................. 607/3 |
| 2005/0149143 | A1 * | 7/2005 | Libbus et al. ............. 607/44 |
| 2005/0154418 | A1 * | 7/2005 | Kieval et al. ............. 607/2 |
| 2006/0004417 | A1 * | 1/2006 | Rossing et al. ............ 607/9 |

(Continued)

FOREIGN PATENT DOCUMENTS

EP 897690 2/1999

OTHER PUBLICATIONS

A Nano Pressure Sensor: Zinc-oxide nanowires that respond electrically when bent could be used to measure minute forces & pressure Prachi Patel-Predd (Technology Review) Mar. 6, 2007.

*Primary Examiner*—George Manuel
*Assistant Examiner*—Shubatra Narayanaswamy
(74) *Attorney, Agent, or Firm*—Patterson Thuente Christensen Pedersen, P.A.

(57) ABSTRACT

An apparatus and a system can chronically and automatically measure a physiologic parameter associated with the high pressure side of the vasculature and/or regulate blood pressure based upon the measured parameter. The apparatus may be made up of a transducer, a baroreflex activation device having one or more electrodes, and a lead having two or more conductors. The system can measure a physiologic parameter and selectively administer a therapy, such as, for example, electro-stimulation of baroreceptors, based upon the measurement. The transducer for measuring the physiologic parameter can be chronically implanted in the high-pressure side of the vasculature. The implantation method may include intravascularly positioning the transducer in the external carotid artery in such a way that the transducer is first introduced into the arterial vasculature through the superior thyroid artery.

12 Claims, 7 Drawing Sheets

U.S. PATENT DOCUMENTS

2006/0196277 A1 9/2006 Allen et al.
2006/0287700 A1 12/2006 White et al.
2007/0191904 A1 8/2007 Libbus et al.

* cited by examiner

METHOD AND SYSTEM FOR IMPLANTABLE PRESSURE TRANSDUCER FOR REGULATING BLOOD PRESSURE

FIELD OF THE INVENTION

The present invention relates generally to implantable medical devices. More particularly, the present invention relates to a chronically implanted apparatus that can regulate blood pressure in response to an integrated measurement of a physiologic parameter and to a method for implanting a blood pressure transducer in the vasculature.

BACKGROUND OF THE INVENTION

Hypertension is a condition characterized by prolonged periods of high blood pressure. Hypertension can lead to an enlarged or damaged heart (hypertrophy) and, eventually, heart failure. Though treatable, hypertension is the primary cause of death for tens of thousands of patients per year in the United States. Hypertension is also listed as a primary or contributing cause of death for hundreds of thousands of patients per year in the United States and affects an estimated 65 million people in the United Sates alone. Therefore, hypertension is a serious health problem necessitating significant research and development of effective treatment.

Blood pressure typically becomes elevated when resistance to blood flow increases. Increased resistance to blood flow can be caused by a variety of factors, including constriction of blood vessels and excessive fluid in the blood. For example, when blood vessels constrict due to plaque build-up on the lining of arterial walls, additional force is required to pump the same volume of blood through the blood vessels. Similarly, when fluid levels in the blood stream increase, additional force is required to pump blood throughout the body to meet the body's needs. The additional force required to maintain a sufficient volumetric flow rate of blood within a constricted space or in a diluted media increases blood pressure.

The body can generally tolerate short periods of increased blood pressure by activating a temporary autonomic response that causes blood pressure to decline. Specifically, the body's autonomic response inhibits the sympathetic nervous system and activates the parasympathetic nervous system. In inhibiting the sympathetic nervous system, the brain directs the heart to decrease cardiac output, the kidneys to reduce blood volume by expunging sodium and water, and the arterioles to dilate. In activating the parasympathetic nervous system, the brain relaxes the body's muscles, decreases the rate of respiration, and signals the heart to reduce the frequency of contractions. These physiologic changes can temporarily decrease blood pressure; however, they also produce other effects, such as fatigue and a reduced capacity for exercise.

When blood pressure becomes elevated, the body's autonomic response is triggered by stretch-sensitive mechanoreceptors, or baroreceptors, located in the walls of the heart and various major blood vessels. Rising blood pressure forces blood vessels to expand. This, in turn, causes baroreceptors located in vascular walls to become distended. As baroreceptors become distended, they generate action potentials more frequently, a physiologic process called baroreflex activation. The increased frequency of action potentials signals the brain to activate an autonomic response. In this manner, baroreceptors provide signals to the brain of changes in blood pressure.

The ability of baroreceptors to inform the brain of changes becomes compromised, however, as short-term changes in blood pressure become long-term changes. This is because baroreceptors detect changes in their distension with respect to a normalized state of distension that is constantly being recalibrated based upon a mean arterial pressure. The mean arterial pressure, called the set point, is typically in the range of 70-110 mmHg for normal, or healthy, blood pressure. If blood pressure remains elevated, such as due to hypertension, the set point will eventually recalibrate to a higher level. Similarly, if blood pressure remains low, such as due to hypotension, the set point will eventually calibrate to a lower level. As a result, hypertension desensitizes baroreceptors to high blood pressure, while hypotension desensitizes baroreceptors to low blood pressure. In the case of hypertension, the body's natural ability to lower blood pressure is thereby eroded as elevated blood pressure causes the set point to become normalized at a relatively high mean arterial pressure. As a result, baroreceptors are gradually prevented from initiating an autonomic response to lower dangerously high blood pressure.

If the volume of blood delivered through the vasculature becomes insufficient to meet the body's needs, such as due to arterial constriction or water absorption, the body may initiate a somatic response that increases blood flow by increasing cardiac output and heart rate. Although the rise in blood pressure that follows a somatic response normally poses little threat, it can become dangerous if the ability to initiate an off-setting autonomic response to lower blood pressure has been compromised, such as due to hypertension. When blood pressure remains elevated following a somatic response, resulting myocardial damage to the heart may eventually reduce blood flow and result in progressively destructive somatic responses that leads to heart failure. It is therefore desirable to be able to initiate a reduction of blood pressure when hypertension has compromised the ability of baroreceptors to initiate such a response.

In an effort to treat hypertension, a number of different treatments have been developed. Some of these treatments focus on cause (high blood pressure), while others focus on effect (heart failure). For example, drug treatments have been proposed that reduce blood pressure. This form of treatment is often incompletely effective, however, since some patients may be unresponsive (refractory) to drug therapy. Drug therapy is also often accompanied by unwanted side effects and requires complex treatment regimens. These and other factors contribute to poor patient compliance with medical therapy. The development and administration of drug therapy is also expensive, adding to the high cost of health care already associated with these disorders.

Surgical procedures have also been proposed to treat hypertension. For example, heart transplantation has been proposed for patients who suffer from severe heart failure. Alternatively, a ventricular assist device may be implanted in the chest to increase the pumping action of the heart or an intra-aortic balloon pump may be used to maintain normal heart function for short periods of time. Cardiac resynchronization therapy may be also used to improve the coordination of contractions of the heart. Like drug treatment, however, surgical approaches are very costly. Surgical treatment is also associated with significant patient mortality rates. Moreover, surgical treatment often focuses on the effect of the problem (heart failure) rather than the source of the problem (hypertension), which fails to alter the natural history of the disease. Therefore, there is a need for improved treatments for hypertension.

One approach to treating the cause of hypertension is implanting electrodes capable of electrically stimulating nerves that produce an autonomic response, a function known as baropacing. For example, when the carotid sinus nerve is stimulated, the brain reduces or ceases activation of the sympathetic nervous system, thereby inhibiting the long-term cycle that can exacerbate heart failure. Electrical stimulation of the carotid sinus nerve (baropacing) has previously been proposed as a treatment for angina and high blood by decreasing the workload of the heart. U.S. Pat. No. 6,073,048 to Kieval, et al. discloses a baroreflex modulation system and method of baroreflex activation based on various cardiovascular and pulmonary parameters.

In treating hypertension, an alternative to nerve stimulation is stimulation of baroreceptors. This form of treatment is commonly known as baroreflex activation therapy, or "BAT." In BAT, baroreflex activation can be achieved through an electro-stimulation of baroreceptors generated by implantable electrode assemblies, called baroreflex activation devices. Implantable electrode assemblies for electrotherapy or electro-stimulation are known in the art. U.S. Pat. No. 6,522,926 to Kieval, et al. discloses a baroreflex activation system and method for activating baroreceptors to regulate blood pressure. By treating hypertension through BAT, a coordinated electrical stimulation of baroreceptors produces the same physiologic response produced by baropacing while avoiding direct nerve stimulation.

Effecting a baroreflex response with a baroreflex activation device, such as through baropacing or baroreflex activation therapy, can be achieved by manual activation, by, for example, a physician. Since this form of treatment requires the presence of a physician who can monitor blood pressure at a given time and prescribe the necessary baropacing therapy, it is typically limited to short-term applications. To achieve effective long-term treatment of hypertension, baroreflex activation device capable of effecting a baroreflex response can be coordinated with a clinically implanted transducer that measures a physiologic parameter representative of blood pressure.

Such coordination with an implanted component presents a number of challenges. For example, because of differences in blood pressure between the high-pressure, arterial side of the vasculature and the low-pressure, venous side of the vasculature, it may be desirable to chronically measure blood pressure in the high-pressure side. Implantation into the high-pressure side, however, can involve additional health risks to a patient due to implantation of a medical device in the high-pressure blood vessels. Chronic implantation of leads with pressure sensors has generally been limited to the low pressure side where the medical risks associated with the long term viability of such implants are lower. While implantation of micro-transducers or micro-stimulators that could be used in connection with high-pressure blood vessels has been proposed, there has been a challenge in providing both effective power and communication to such miniature and isolated implants.

There remains a need for a chronically implanted medical device that integrates continuous measurements of a physiologic parameter, such as blood pressure, with selective modulation and/or regulation of blood pressure, as well a minimally-invasive procedure for implanting the device in the high-pressure side of the vasculature.

SUMMARY OF THE INVENTION

An apparatus and a system are disclosed for chronically and automatically measuring a physiologic parameter associated with the high pressure side of the vasculature and/or regulating blood pressure based upon the measured parameter. A method is also disclosed for chronically implanting in the high-pressure side of the vasculature a transducer for measuring a physiologic parameter. In one embodiment, the parameter is representative of blood pressure measured with a transducer implanted in a snipped arterial blood vessel. In another embodiment, the transducer is part of a lead arrangement that stimulates baroreceptors to initiate or otherwise control a baroreflex response.

In one embodiment, the apparatus is made up of a transducer, a baroreflex activation device having one or more electrodes, and a lead having two or more conductors. A similar apparatus that provides the same functionality may also have two or more leads. The transducer, baroreflex activation device, and lead should all be suitable for chronic implantation. The transducer measures a physiologic parameter, such as one that is representative of blood pressure. The transducer also generates a sensor signal that describes the measured physiologic parameter. The baroreflex activation device has an electrode, or an array of electrodes, capable of stimulating a baroreceptors or a patient's baroreflex system. The baroreceptor activation device can selectively stimulate one or more baroreceptors in accordance with instructions received in a therapy signal. The baroreflex activation device and the transducer may be connected to the same end of the lead, typically the distal end, although the baroreflex activation device and the transducer can also be disposed on separate leads. In the case of either a single-lead configuration or multiple-lead configurations, the baroreflex activation and the transducer are individually operably connected to common or separate conducting wires, or conductors, located within the lead. The lead facilitates communication with and provides a conduit for delivering power to the transducer and the baroreflex activation device.

The system can measure any number of physiologic parameters and initiate baroreflex activation to effect a baroreflex response in a number of ways. In an embodiment, baroreflex activation may include baroreflex activation therapy, baropacing, or a combination thereof. In one aspect of the present invention, the system measures a physiologic parameter representative of blood pressure or other blood-related physiologic parameter to determine whether blood pressure has reached a high or low threshold level. Specifically, the transducer could monitor systolic pressure, diastolic pressure, average pressure, pulse pressure, blood volumetric flow rate, blood flow velocity, blood pH, oxygen or carbon dioxide content, pulse rate, mixed venous oxygen saturation, vasoactivity, body temperature, blood composition, or other physiologic parameters that can be measured or detected by a transducer positioned in the vasculature. Based upon measurements of these and other physiologic parameters, the system selectively administers electro-stimulation of baroreceptors. In this manner, the system is able to utilize the body's existing baroreflex activation circuitry of nerves and baroreceptors to reduce blood pressure. In other aspects of the present invention, the transducer may be used with other sensors to measure non-blood related physiologic parameters, such as, for example, nerve activity, tissue activity, body movement, body temperature, activity levels, and respiration.

In one embodiment, as the transducer monitors blood pressure, the transducer generates a sensor signal that correlates to the measured parameter. The lead relays the sensor signal from the transducer to a control unit. The control unit receives and interprets the sensor signal. Based upon an algorithm or circuitry that determines whether the sensor signal indicates that a threshold blood pressure has been reached, the control unit may generate a therapy signal. The control unit can also provide power for the system. The lead relays the therapy signal from the baroreflex activation device, which causes an electrode or an array of electrodes to stimulate baroreceptors.

In this manner, the system can reduce or increase blood pressure by selectively inducing baroreceptors to initiate baroreflex activation.

In one embodiment, a method of implanting an apparatus in accordance with the present invention utilizes existing vasculature structures. The apparatus is typically disposed on high-pressure vasculature, such as an artery. Although this embodiment is described primarily with reference to implantation in or on the carotid sinus and external carotid artery, this embodiment can be adapted to function in connection with any vasculature structure containing tissue capable of influencing a patient's baroreflex system. In a typical procedure in accordance with this embodiment, the transducer is intravascularly implanted in the external carotid artery in such a way that the transducer is first introduced into the arterial vasculature through the superior thyroid artery. This may eliminate the need to access the implantation site through a distal arterial blood vessel. The baroreflex activation device is typically perivascularly implanted on or near the carotid sinus in this embodiment.

It should be understood that the intention is not to limit the present invention to any particular embodiments described. On the contrary, the intention is to cover all modifications, equivalents, and alternatives falling within the spirit and scope of the present invention as defined by the appended claims.

BRIEF DESCRIPTION OF THE DRAWINGS

This invention may be more completely understood in consideration of the following detailed description of various embodiments of the invention in connection with the accompanying drawings, in which.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Overview

Figure 1:
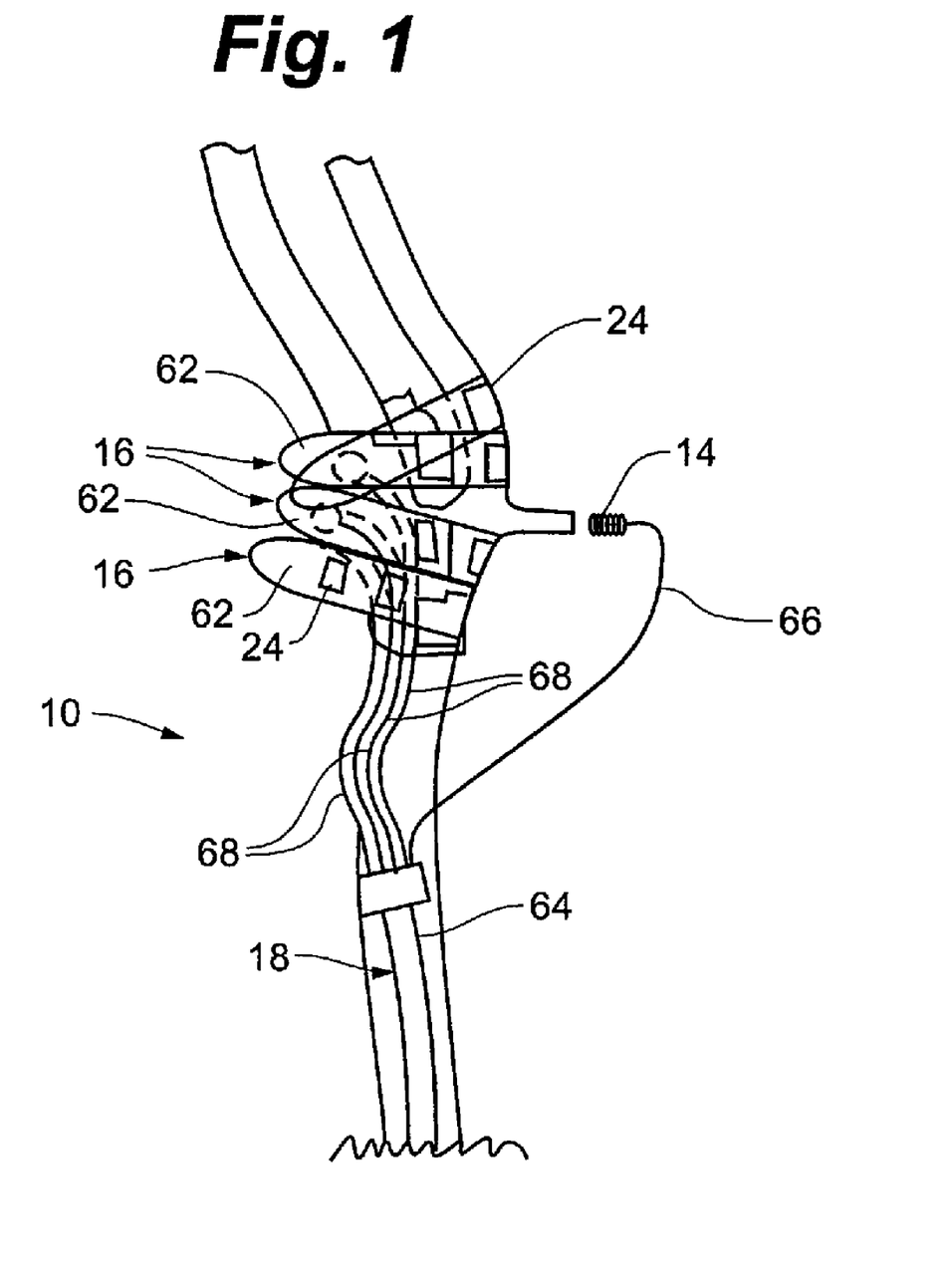
FIG. 1 is a schematic illustration of an implanted medical device according to the present invention.
Figure 2:
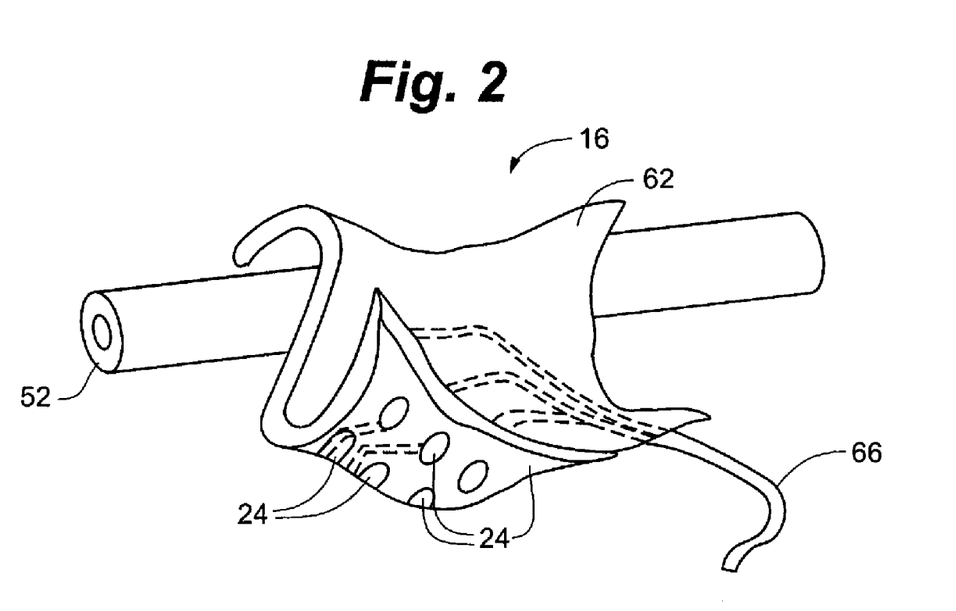
FIG. 2 is a schematic illustration of the function of a closed-loop feedback mechanism according to an embodiment of the present invention.
Figure 3:
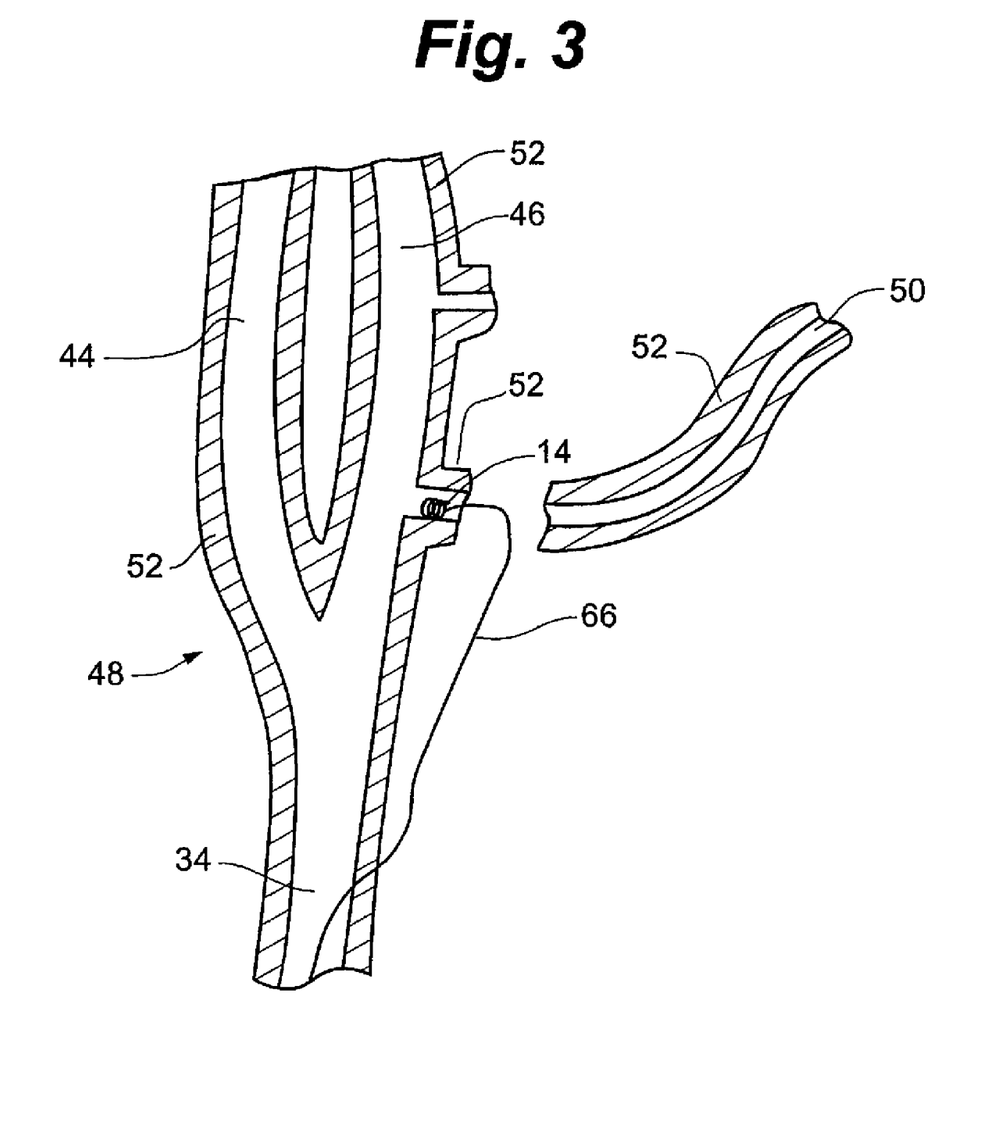
FIG. 3 is a schematic illustration of the function of a closed-loop feedback mechanism according to another embodiment of the present invention.

Referring to FIGS. 1-3, the present invention is directed to an implanted medical device 10, a system 12 for operating implanted medical device 10, and method for implanting medical device 10. Medical device 10 generally comprises transducer 14, baroreflex activation device 16, and lead 18. In operation, medical device 10 is connected to control unit 20 as part of system 12. To address the problems of hypertension, heart failure, and other cardiovascular disorders, as well as certain renal disorders, a physiologic parameter, such as blood pressure. Depending upon an interpreted value of the measured physiologic parameter, baroreflex system 21 can be selectively stimulated so as to initiate a baroreflex response such as, for example, through baroreflex activation therapy or baropacing, or a combination thereof.

Any number of physiologic parameters from different areas of the body may be measured. In an embodiment, the present invention can measure blood pressure inside an area of the body's vasculature. When the blood pressure reaches a pre-determined threshold, the body's natural response to elevated blood pressure is minimized by activating baroreceptors 22, which are depicted schematically in FIGS. 4-5. Whereas chronically elevated blood pressure gradually erodes the natural effectiveness of baroreceptors 22 by increasing the threshold blood pressure at which baroreceptors 22 are activated, a constant blood pressure threshold may be set and maintained. Blood pressure may be reduced by selectively stimulating baroreceptors 22 even after the mean arterial pressure, or set point, of baroreceptors 30 has been normalized to a relatively high median arterial pressure.

Referring to FIG. 1, control unit 20 is linked to transducer 14 and baroreflex activation device 16 via lead 18 in an embodiment. Transducer 14 optionally measures a physiologic parameter. Lead 18 can communicate to control unit 20 a sensor signal correlating the measured physiologic parameter. Control unit 20 interprets the sensor signal and may generate a therapy signal. Lead 18 relays the therapy signal to the baroreflex activation device 16. The therapy signal activates, deactivates, or otherwise modulates electrodes 24 in the baroreflex activation device 16, which typically results in activation of baroreceptors 22.

In an example embodiment, an implanted closed-loop feedback mechanism may be operated to treat hypertension through baroreflex activation therapy. In this embodiment, transducer 14 measures blood pressure. As previously noted, transducer 14 can also measure non-blood related physiologic parameters. Lead 18 communicates this measurement as a sensor signal representing a value of the measured physiologic parameter. Control unit 20 interprets the therapy signal according to an algorithm that determines whether the value indicates that a threshold blood pressure has been reached. If the threshold value has been reached, control unit 20 generates a therapy signal that is communicated by lead 18 to baroreflex activation device 16. Depending upon the blood pressure measured by transducer 14 and the algorithm used to interpret the sensor signal, therapy signal can cause electrodes 24 to stimulate baroreceptors 22 in a manner that optimally reduces blood pressure. In this manner, real-time monitoring and treatment of hypertension and other physiologic conditions, as in other embodiments, may be provided.

Anatomy/Physiology

Figure 6:
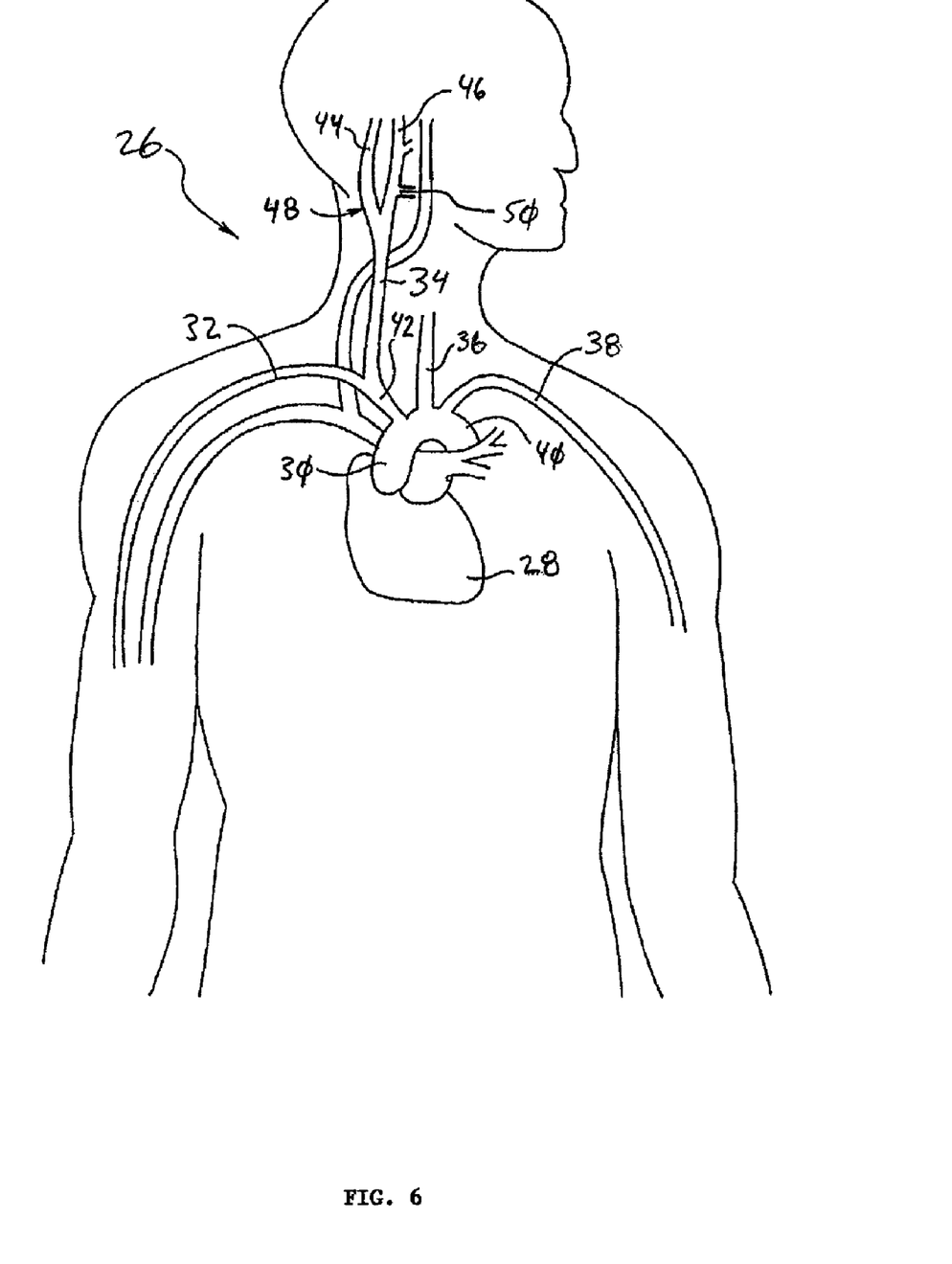
FIG. 6 is a schematic illustration of the upper torso of a human body showing the major arteries and veins and associated anatomy.

Referring to FIG. 6, a schematic illustration of the upper torso of human body 26 shows major blood vessels located in the upper torso of human body 26. The left ventricle of heart 28 pumps oxygenated blood up into aortic arch 30. Right subclavian artery 32, right common carotid artery 34, left common carotid artery 36, and left subclavian artery 38 branch off aortic arch 30 proximal to the descending thoracic aorta 40. Brachiocephalic artery 42 connects right subclavian artery 32 and right common carotid artery 34 to aortic arch 30. Right common carotid artery 34 bifurcates into right external carotid artery 44 and right internal carotid artery 46 at right carotid sinus 48. Branching off right internal carotid artery 46 proximal to right carotid sinus 48 is right superior thyroid artery 50. Although not shown for purposes of clarity only, left common carotid artery 36 similarly bifurcates into the left external carotid artery and the left internal carotid artery at the left carotid sinus.

Some of these blood vessels, such as internal and external carotid arteries 44, 46 and carotid sinus 28, contain baroreceptors. Baroreceptor signals in the arterial vasculature are used to activate a number of body systems which collectively may be referred to as the baroreflex system. For the purposes of the present invention, it will be assumed that the "receptors" in the venous and cardiopulmonary vasculature and heart chambers function analogously to the baroreceptors in the arterial vasculature, but such assumption is not intended to limit the present invention in any way. In particular, the methods described herein will function and achieve at least some of the stated therapeutic objectives regardless of the precise and actual mechanism responsible for the result. Moreover, the present invention may activate baroreceptors, mechanoreceptors, pressoreceptors, stretch receptors, chemoreceptors, or any other venous, heart, or cardiopulmonary receptors which affect the blood pressure, nervous system activity, and neurohormonal activity in a manner analogous to baroreceptors in the arterial vasculation. For convenience, all such venous receptors will be referred to collectively herein as "baroreceptors" or "receptors" unless otherwise expressly noted.

While there may be small structural or anatomical differences among various receptors in the vasculature, for the purposes of the present invention, activation may be directed at any of these receptors and/or nerves and/or nerve endings from these receptors so long as they provide the desired effects. In particular, such receptors will provide afferent signals, i.e., signals to the brain, which provide the blood pressure and/or volume information to the brain. This allows the brain to cause "reflex" changes in the autonomic nervous system, which in turn modulate organ activity to maintain desired hemodynamics and organ perfusion. Activation of the baroreflex system may be accomplished by stimulating such receptors, nerves, nerve fibers, nerve endings, or any combination thereof.

Figure 4:
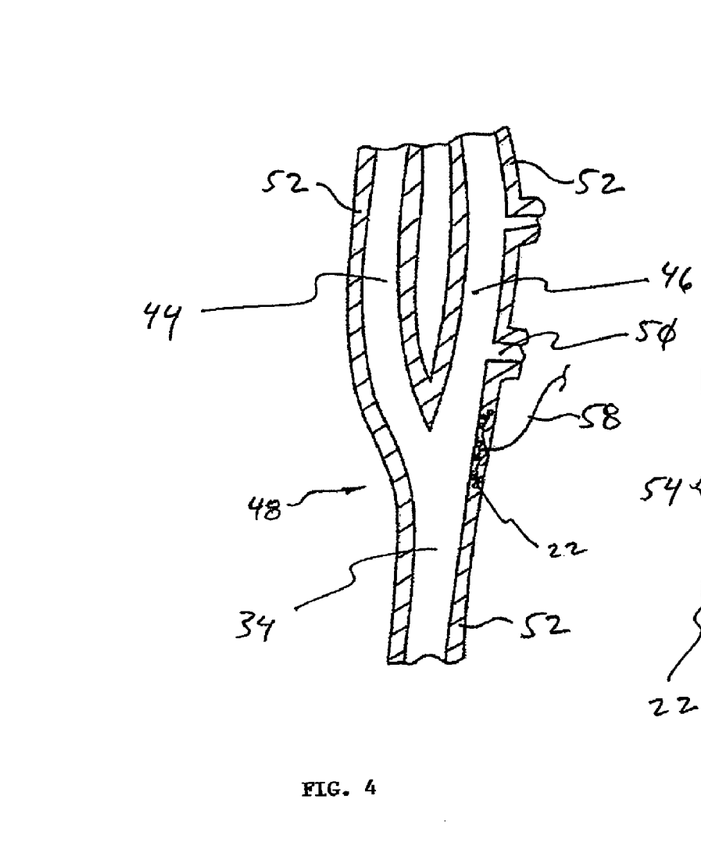
FIG. 4 is a schematic illustration of a portion of a vascular wall containing baroreceptors.
Figure 5:
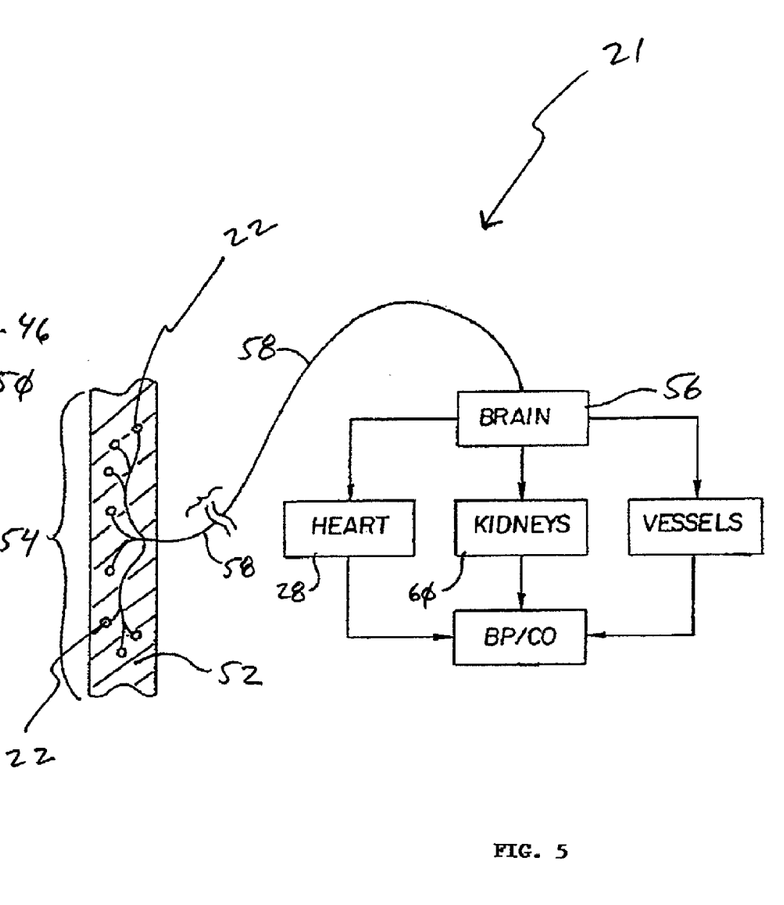
FIG. 5 is a schematic illustration of a baroreflex system.

As depicted in FIGS. 3-4, baroreceptors 22 are located in vascular wall 52 of various arterial structures and veins, the pulmonary vasculature, and the chambers of heart 28. Baroreceptors 22 are a type of stretch receptor used by the body to sense blood pressure and blood volume. An increase in blood pressure or volume causes vascular walls 52 to return to their original size. Because baroreceptors 22 are located within vascular walls 52, baroreceptors 22 are able to sense deformation of vascular walls 52, which is indicative of a change in blood pressure. Baroreceptors 22 located in the carotid sinus 48, external carotid artery 44, internal carotid artery 46, and aortic arch 30, and internal carotid artery 46, among other high-pressure vasculature, play a significant role in sensing blood pressure.

Action potentials generated by baroreceptors 22 in the arterial vasculature activate a number of body systems, including the baroreflex system. FIG. 4 shows a schematic illustration of baroreceptors 22 in vascular wall 52 and a schematic flow chart of the baroreflex system 21. Baroreceptors 22 are profusely distributed within vascular walls 52 and generally form arbor 54. Baroreceptors 52 are so profusely distributed and arborized within vascular wall 54 that discrete baroreceptor arbors 54 are not readily discernable. To this end, those skilled in the art will appreciate that baroreceptors 22 shown in FIGS. 3-4 are primarily schematic for purposes of illustration and discussion. Baroreceptor arbor 54 comprises a plurality of baroreceptors 22, each of which transmits baroreceptor signals to brain 56 via nerve 58. Brain 56 is thereby able to detect changes in blood pressure, which is indicative of cardiac output, and effect physiologic changes that affect heart 28, kidneys 60, among other high pressure vascular and blood vessels.

Transducer

Transducer 14 can be used to measure any number of physiologic parameters. In an example embodiment, transducer 14 measures a physiologic parameter representative of blood pressure. Examples of a physiologic parameters that may indicate an elevation in blood pressure include ECG, systolic pressure, diastolic pressure, average pressure, pulse pressure, blood volumetric flow rate, blood flow velocity, blood pH, oxygen or carbon dioxide content, pulse rate, mixed venous oxygen saturation, vasoactivity, nerve activity, tissue activity, body movement, body temperature, activity levels, respiration, composition, or any other physiologic parameter representative of blood pressure. Examples of a suitable transducer 14 include an ECG electrodes, a piezoelectric pressure transducer, an ultrasonic flow velocity transducer, an ultrasonic volumetric flow rate transducer, a thermodilution flow velocity transducer, a capacitive pressure transducer, a membrane pH electrode, an optical detector, tissue impedance, a pulse oximetry sensor, a strain gauge, or a nanotube. Such transducers are known in the art and are described, for example, in the following United States Patents and Published Applications: U.S. Pat. No. 7,147,604 to Allen, et al., U.S. Pat. No. 7,029,447 to Rantala, U.S. Pat. No. 6,652,464 to Schwartz, et al., U.S. Pat. No. 6,645,143 to VanTassel, et al., U.S. Pat. No. 6,522,926 to Kieval, et. al, U.S. Pat. No. 6,360,123 to Kimchi, et al., U.S. Pat. No. 6,277,078 to Porat, et al., U.S. Pat. No. 6,024,704 to Meador, et al., U.S. Pat. No. 5,063,937 to Ezenwa, et al., U.S. Pat. No. 5,003,976 to Alt, U.S. Pat. No. 4,562,843 to Djordjevich, et al., U.S. Pat. No. 4,485,813 to Anderson, et al., U.S. Pat. No. 3,996,925 to Djordjevich., Pub. No. US 2006/0287700 A1 to White, et al., and Pub. No. 2006/0004417 A1 to Rossing, et al. European Patent Application No. EP 897,690 and an article entitled "A Nano Pressure Sensor: Zinc-oxide nanowires that respond electrically when bent could be used to measure minute forces and pressure," Prachi Patel-Predd (Technology Review, Mar. 6, 2007), all of which disclose relevant transducers, the disclosures of which are hereby incorporated by reference only in relation to the figures and detailed description and excluding any terms expressly defined therein.

Depending upon the desired use of transducer 14, transducer 14 may be implanted in any number of ways. Transducer 14 may be implanted inside the body, as for example, in or on an artery, a vein, or a nerve. Transducer 14 may also be disposed outside the body. In one embodiment, transducer 14 may be implanted transluminally, laproscopically, or subcutaneously. Transluminal implantation of transducer 14 may be desired when the physiologic parameter is to be measured acutely and a non-invasive surgical implantation procedure is preferred. In another embodiment, transducer 14 may be implanted in a manner that permits chronic measurement of the desired physiologic parameter. Chronic implantation can be achieved by positioning transducer 14 in a high-pressure vasculature, such as a chamber of heart 28, aortic arch 30, external carotid artery 44, subclavian artery 32, brachiocephalic artery 42, or other major arterial blood vessel. In an example embodiment, transducer 14 is implanted inside a branch of the external carotid artery 44, such as, for example, superior thyroid artery 50.

When transducer 14 measures a physiologic parameter, transducer 14 generates a sensor signal. As described in U.S. Pat. No. 6,024,704 to Meador, et al., the sensor signal generated by transducer 14 preferably corresponds to the measured physiologic parameter or a reference value from which the physiologic parameter can be accurately derived. In one embodiment, transducer 14 only generates a sensor signal when the measured physiologic parameter reaches a predetermined threshold or occurs within a certain range. In other embodiments, transducer 14 generates a sensor signal representative of the measured physiologic parameter regardless of the measurement. In these embodiments, the sensor signal may be generated in intervals or in a pre-determined sequence. In one embodiment, transducer 14 generates the sensor signal continuously such that the physiologic parameter can be measured continuously. Changes in the physiologic parameter, such as elevations in blood pressure, can thereby be detected simultaneously with the changes as they occur. In another embodiment, transducer 14 generates the sensor signal periodically such that the physiologic parameter can be measured periodically.

Baroreflex Activation Device/Electrodes

Whereas transducer 14 measures a physiologic parameter, baroreflex activation device 16 initiates a physiologic response. Upon receiving a therapy signal, baroreflex activation device 16 activates baroreceptors 22. Baroreflex activation device 16 may comprise a wide variety of devices that utilize electrical or non-electrical means to activate baroreceptors 22. Thus, in response to detection by transducer 14 of a physiologic parameter, such as elevated blood pressure, baroreflex activation device 16 may activate baroreceptors 22. In turn, activation of baroreceptors 22 initiates an autonomic response that inhibits the sympathetic nervous system and stimulates the parasympathetic nervous system.

Baroreflex activation device 16 may be positioned where baroreceptors 22 significantly impact or otherwise affect baroreflex system 21. Multiple baroreflex activation devices 16 may also be used on a patient. Such baroreceptors 22 may be located in heart 28 and throughout the arterial vasculature, such as in aortic arch 22, external carotid artery 44, carotid sinus 48, subclavian artery 32, brachiocephalic artery 42, and other high pressure blood vessels. Baroreflex activation device 16 may be implanted such that baroreflex activation device 16 is positioned immediately adjacent baroreceptors 22. Alternatively, baroreflex activation device 16 may be outside the body such that device 16 is positioned a short distance from, but proximate to, baroreceptors 22. In an example embodiment, baroreflex activation device 16 is implanted in or proximal to carotid sinus 48.

Figure 7:
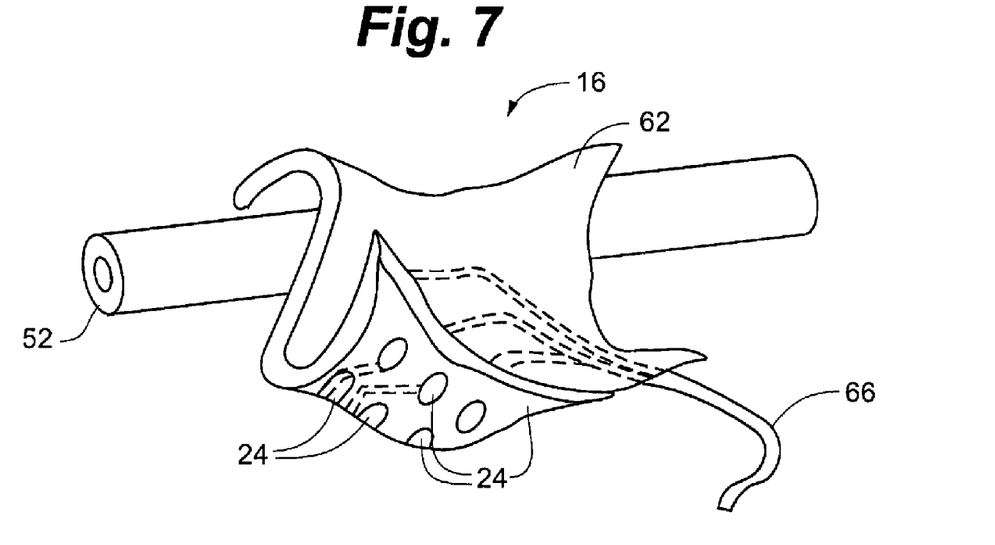
FIG. 7 is schematic illustration of a baroreflex activation device having an array of electrodes.

Referring to FIGS. 1 and 7, baroreflex activation device 16 generally comprises an array of electrodes 24 and flexible elastomeric base 62. The array of electrodes 24 encompasses many possible configurations, shapes, sizes, and arrangements of electrodes 24. Electrodes 24 may be grouped together in regions such that all or part of a region of electrodes 24 may be activated simultaneously. Flexible elastomeric base 62 has a pair of opposing major surfaces and assists in securing baroreflex activation device 16 such that electrodes 24 are operably aligned with baroreceptors 22. Flexible elastomeric base 62 is designed to conform at least partially around an outer surface of an artery or similar structure when baroreflex activation device 16 is installed thereupon. A plurality of electrodes 24 are provided on or near at least one of base surfaces. Electrodes 24 are thereby brought into contact with a blood vessel when baroreflex activation device 16 is wrapped around the blood vessel, as depicted in FIG. 7. In an example embodiment, electrodes are brought into contact with carotid sinus 58 when baroreflex activation device 16 is wrapped around carotid sinus 58. Just as electrodes 24 may be varied in size and shape, flexible elastomeric base 62 may comprise numerous possible shapes, configurations, and arrangements. Additional information about electrode designs and configurations can be found in U.S. Published Application No. 2007/0021796 A1 to Kieval, et al., the disclosure of which is herein incorporated by reference in its entirety.

Lead

Transducer 14 and baroreflex activation device 16 are disposed on the distal end of lead 18. Lead 18 may be coupled to transducer 14 and baroreflex activation device 16 in any number of configurations. Lead 18 typically comprises a minimum of one signal-conducting wire surrounded by insulative sheath 64. Lead 18 is able to relay sensor and therapy signals as well as provide a conduit for the delivery of power.

Lead 18 generally includes at least two conductors 66, 68, but may include more than two. Suitable connections include, but are not limited to, individual conductors 66, 68 embedded within flexible elastomeric base 62, conductive wires, or other similar connection methods as will be apparent to one skilled in the art. At least one conductor 66 operably connects control unit 20 to transducer 14 and is configured to communicate a sensor signal from transducer 16. Similarly, at least one conductor 68 operably couples control unit 20 to baroreflex activation device 16 and can communicate a therapy signal to baroreflex activation device 16. Conductor 68 may be coupled to baroreflex activation device 16 at electrode 24.

When baroreflex activation device 16 contains a plurality of electrodes 24, electrodes 24 may be coupled to lead 18 in any number of ways. Generally, a single lead 18 is connected to transducer 14 and baroreflex activation device 16. In an example embodiment, as depicted in FIG. 1, transducer 18 and baroreflex activation device 16 are disposed on lead 18 at the same end, typically a distal end. The proximal end may be connected to control unit 20. In another embodiment, conductors 66, 68 are operably connected to transducer 14 and baroreflex activation device 16 with separate leads 18.

In addition to facilitating communication, lead 18 may also serve as a conduit for power. Connecting control unit 20 to transducer 14 and baroreflex activation device 16 with conductors 66, 68 reduces the total power that must be provided by control unit 20 as compared to wireless systems. By reducing power requirements, the overall size of various components of system 12 can be reduced, which can facilitate implantation procedures. A reduction in power requirements also permits battery or other chronically implantable power source to provide sufficient power for chronic implantation of the entire system 12. Utilization of lead 18 to deliver power may maximize longevity of transducer 14 in continuously measuring a physiologic parameter, of control unit 20 in interpreting sensor signals and generating therapy signals, and of baroreflex activation device 16 in stimulating baroreceptors 22.

Referring to FIGS. 2-3, conductor 68 may operably connect baroreflex activation device 16 to control unit 20 directly or through a switching mechanism 69, such as is described in U.S. Published Application No. 2007/0021796 A1 to Kieval, et al, which may or may not be physically located within control unit 20. When baroreflex activation device 16 is coupled to the switching mechanism 69, at least one electrode 24 will comprise an anode and at least one electrode 24 will comprise a cathode. Generally, switching mechanism 69 activates desired electrodes 24 by opening or closing individual switches based upon information received from control system 20. The decision of which electrodes 24 to energize may come from an algorithm stored in memory 70, user input or transducer 14.

A problem often associated with the implantation of wired medical devices is the degradation of conductors 66, 68 due to friction. Such degradation commonly results from normal physiologic activity of the patient. When device 10 is implanted relatively superficially, such as in or around the carotid sinus 48, patient interference with device 10 can also accelerate degradation due to friction between conductors 66, 68. To solve this problem, in one embodiment the same lead 18 that communicates a sensor signal or therapy signal may connect transducer 14 and baroreflex activation device 16 to a power source and control unit 20. By combining the functions of signal communication and power delivery in lead 18, the number of wires implanted in a patient can be reduced. This, in turn, reduces the likelihood of degradation of conductors and, therefore, increases the efficacy and longevity of device 10.

Communication of the sensor and therapy signals and delivery of power may occur over a single lead or over multiple leads. In an example embodiment, communication of the sensor and therapy signals and power delivery are multiplexed over single lead 18. In another embodiment, communication of sensor and therapy signals and delivery of power may be multiplexed over a single lead 18.

In embodiments in which the power delivery and signal communication are multiplexed, the sensor signal, therapy signal, and power delivery may be conducted over the same set of conductors 66, 68 or a different set of conductors. Generally, however, the sensor signal, the therapy signal, and power delivery may be conducted over the same set of conductors 66, 68. Any form of multiplexing may be employed, including, but not limited to, time-division multiplexing, frequency-division multiplexing, or other type of multiplexing. Appropriate multiplexer and de-multiplexer devices may be included for this purpose.

In an example embodiment, the bidirectional communication of the sensor and therapy signals that is necessitated by multiplexing is accomplished by communicating data signals between therapy pulses. Generally, the data signals for baroreflex activation are sub-threshold. Such sub-threshold signals can include sub-threshold voltage, sub-threshold pulse width, or high-frequency. In another embodiment, the bidirectional communication that is necessitated by multiplexing is accomplished by communicating data signals during communication of therapy pulses.

Control Unit

Referring to FIGS. 2-3, an embodiment of a system 12 whereby control unit 20 is in communication with and provides power to transducer 14 and baroreflex activation device 16 is disclosed. System 12 provides a closed-loop feedback mechanism that stimulates a physiologic response in response to a measured physiologic parameter. Generally, control unit 20 is responsible for coordinating the measurement of a physiologic parameter with the delivery of an appropriate response. Control unit 20 receives sensor signal from transducer 14. Based upon an algorithmic interpretation by processor 72 of information relating to the measured physiologic parameter represented by the sensor signal, for example, control unit 20 may generate a therapy signal that instructs baroreflex activation device 16 to perform a certain function. In this way, control unit 20 may provide a feedback mechanism for inducing a physiologic change in response to a physiologic condition. In an example embodiment, control unit 20 can cause baroreceptors 22 to be stimulated when an elevated blood pressure is detected.

By way of example, control unit 20 may include a control block 74 comprising processor 72 and memory 70. Control unit 20 is connected to transducer 14 and baroreflex activation device 16 by way of lead 18. Control unit 20 thereby receives a sensor signal from transducer 14 by way of lead 18 and also transmits a therapy signal to baroreflex activation device 16 by way of the same lead 18.

Memory 70 may contain data relating to the sensor signal, the therapy signal, and values and commands provided by an input device. Memory 70 may also include software containing one or more algorithms defining one or more functions or relationships between the sensor signal and the therapy signal. In response to a sensor signal or a mathematical derivative thereof, the algorithm may generate a therapy signal that activates baroreflex activation device 16 or electrodes 24. Alternatively, the algorithm may deactivate baroreflex activation device 16 or electrodes 24 or dictate that no therapy signal be generated in response to a sensor signal. In an example embodiment, when a value represented by the sensor signal rises above a predetermined threshold value, the algorithm dictates that a therapy signal be generated that initiates baroreflex activation to effect a particular baroreflex response. Similarly, when a value represented by the sensor signal falls below a predetermined threshold value, the algorithm may dictate that no action be taken or that a therapy signal be generated that inhibits baroreflex activation to effect a particular baroreflex response. As previously noted, baroreflex activation may include baroreflex activation therapy, baropacing, or a combination thereof. Alternatively, similar functionality may be achieved by use of analog signals and analog circuitry, or a combination of digital and analog circuitry.

Control unit 20 may generate a therapy signal based upon an internal feedback loop or commands received from an external source. In one embodiment, control unit 20 operates as an open loop utilizing reprogramming commands received by input device. Programming commands received from the input device may directly influence the therapy signal, the output activation or other threshold parameters, for example, the software, and related algorithms contained in memory 70. The treating physician or patient may provide commands to input device. In another embodiment, control unit 20 operates as a closed loop utilizing feedback from transducer 14.

The therapy signal generated by the control unit 20 may be continuous, periodic, alternating, episodic, variable, or a combination thereof, as dictated by an algorithm contained in memory 70. Referring to FIG. 3, the therapy signal may be transmitted through switching mechanism 69 to selectively activate electrodes 24 located in baroreflex activation device 16. Switching mechanism 69 may be integrated within control unit 20 or into or onto baroreflex activation device 16.

In an example embodiment, control unit 20 may also comprise a battery that provides a power source. The battery should provide sufficient power to enable control unit 20 to interpret sensor signal and generate a therapy signal, transducer 14 to measure a desired physiologic parameter and generate a representative sensor signal, and baroreflex activation device 16 to stimulate baroreceptors 22 based upon therapy signal.

In one embodiment, power is provided by a full-wave rectifier. In this embodiment, the full-wave rectifier may provide sufficient power to enable control unit 20 to interpret sensor signal and generate a therapy signal, transducer 14 to measure a desired physiologic parameter and generate a representative sensor signal, and baroreflex activation device 16 to stimulate baroreceptors 22 based upon therapy signal. Full-wave rectification of therapy pulses will thereby continue to power transducer 14 even if the therapy polarity is inverted. In another embodiment, a half-wave rectifier can be used to provide power if the polarity of the therapy signal cannot be inverted.d Implantation Method Transducer 14 may be implanted in any number of ways that enable a physiologic parameter, such as a physiologic parameter representative of blood pressure, to be measured. In one embodiment, transducer 14 is preferably anchored to vascular tissue. For example, transducer 14 may be positioned inside or outside a blood vessel, within a vascular wall 52, or in a chamber or a wall of heart 28.

In an example embodiment, transducer 14 is implanted in a high-pressure side of the vasculature. Blood pressure in arterial blood vessels is typically higher than in venous blood vessels of similar size and position within the body. This higher blood pressure can make sensing and monitoring blood pressure in arterial blood vessels easier and more accurate than measuring blood pressure in venous blood vessels. Due to relatively high pressures in arterial blood vessels, however, implantation of transducer 14 in an arterial blood vessel may expose a patient to additional risks and complications from the implantation procedure. For example, introduction of transducer 14 into arterial blood vessel can lead to a distal or local arterial embolism. Dislodgment or separation of transducer 14 can also lead to blood vessel blockage or other damage. Furthermore, lengthy implantation procedures can exacerbate blood loss.

A common entry point during surgery into the arterial vasculature is through the femoral artery because it provides a relatively accessible, low-pressure, and navigable arterial blood vessel. The distal location of the femoral artery with respect to high-pressure blood vessels that contain baroreceptors 22, however, increases the complexity of the implantation procedure as well as the risk of harm when using the femoral artery an a point of entry into the vasculature. The implantation method disclosed by this embodiment reduces some of the hazards and difficulties associated with intravascularly positioning transducer 14 within arterial vasculature containing baroreceptors 22. Specifically, the method reduces the invasiveness of implanting transducer 14 in a major arterial blood vessel by introducing transducer 14 into a minor arterial blood vessel proximal to the implantation site.

Figure 8:
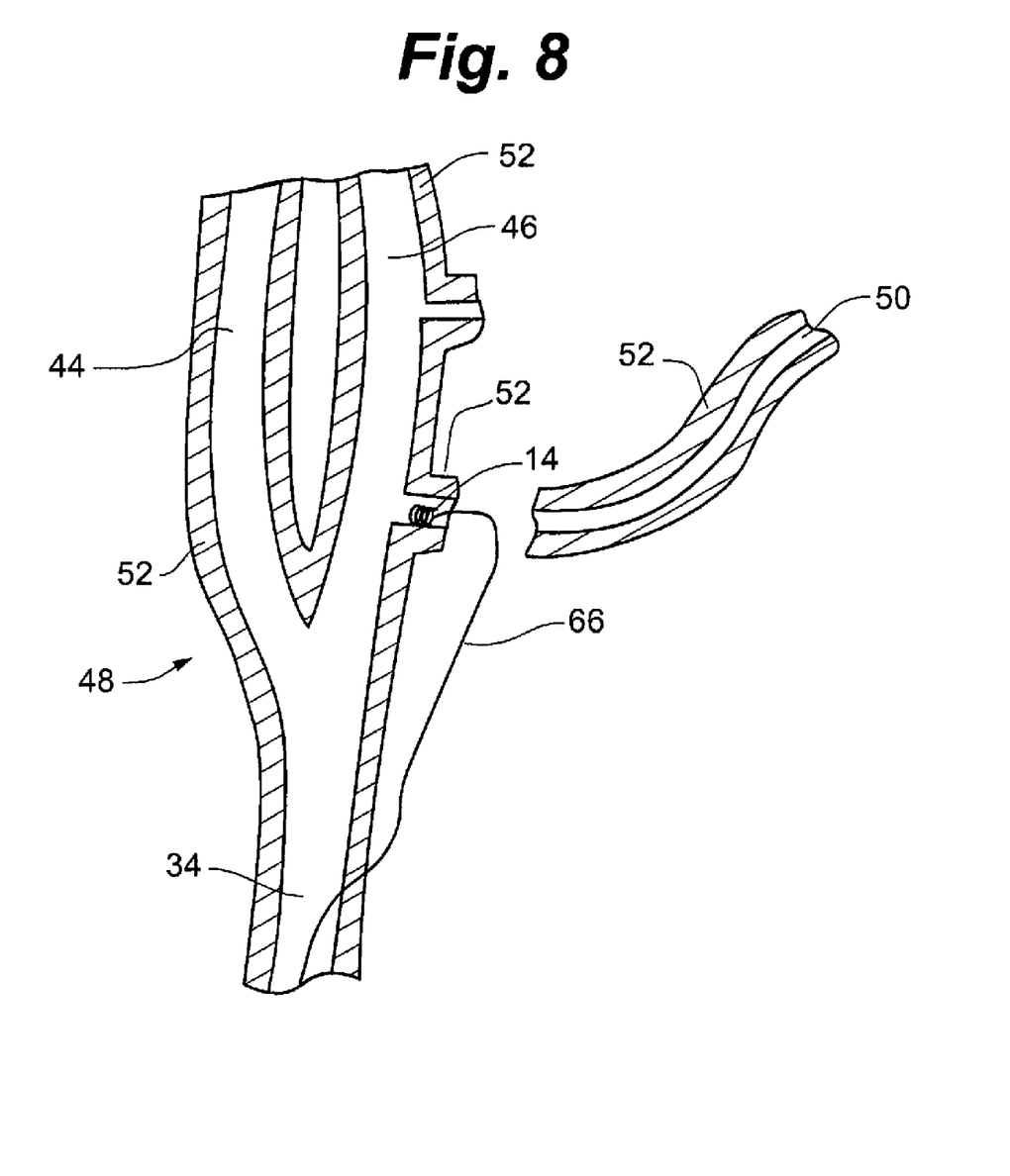
FIG. 8 is a schematic illustration of the vasculature featured in an implantation method according to an embodiment of the present invention.

Generally, when implanting transducer 14 according to this embodiment, an incision is first made in a minor blood vessel that branches off of the major blood vessel, such as superior thyroid artery 50. As depicted in FIGS. 1 and 8, this creates a point of access into the major blood vessel that is relatively near the major blood vessel and in a manner that does not harm the major blood vessel. Transducer 14 is then fed into the major blood vessel by way of the minor blood vessel. This may be advantageous in several respects. First, the minor blood vessel that provides an access point into the major blood vessel may be commonly sacrificed during surgical procedures to position the transducer 14 onto the major blood vessel. Second, introduction of the transducer 14 into the vasculature through a site proximal to the implantation site reduces the likelihood of an embolic event or other complication that could result in a stroke.

In an example embodiment, transducer 16 is implanted in external carotid artery 46 via superior thyroid artery 50. Using this method, superior thyroid artery 50 is sacrificed to provide access into external carotid artery 46 or carotid sinus 48, as depicted in FIG. 8. Since there is a greater risk of an embolic event when the surgical implantation procedure requires significant navigation of arterial blood vessels, the method of implantation of this embodiment may be beneficial when the desired implantation site is an arterial blood vessel near heart 28, such as for implantation of transducer 14 into external carotid artery 46. Further, in the event of an embolic event, external carotid artery 46 directs blood to the face of a patient, minimizing the severity of potential damage occurring after an embolic event.

In contrast to the intravascular implantation of the transducer 14, baroreflex activation device 16 is generally implanted perivascularly. During implantation of baroreflex activation device 16, the device is wrapped around a blood vessel or other tissue having baroreceptors 22 and secured in a suitable manner. Additional information about methods of securing mechanisms can be found in U.S. Published Application No. 2007/0038262 A1 to Kieval, et al., the disclosure of which is hereby incorporated by reference in its entirety. In an example embodiment, baroreflex activation device 16 is wrapped around carotid sinus 48.

When circumferentially installed around a blood vessel such as carotid sinus 48, baroreflex activation device 16 may be wrapped around the blood vessel so that all or most of the outer surface of the structure can be covered, as depicted in FIG. 7. In one embodiment, electrodes 24 are in direct contact with the outer surface of the blood vessel. In another embodiment, electrodes 24 may be located within flexible base 62 such that electrodes 24 are not in direct contact with the blood vessel. In an example embodiment, electrodes 24 of baroreflex activation device 16 are positioned in close proximity to the outer surface of the blood vessel.

The embodiments above are intended to be illustrative and not limiting. Additional embodiments are within the claims. In addition, although the present invention has been described with reference to particular embodiments, those skilled in the art will recognize that changes can be made in form and detail without departing from the spirit and scope of the invention. Any incorporation by reference of documents above is limited such that no subject matter is incorporated that is contrary to the explicit disclosure herein.

For purposes of interpreting the claims for the present invention, it is expressly intended that the provisions of Section 112, sixth paragraph of 35 U.S.C. are not to be invoked unless the specific terms "means for" or "step for" are recited in a claim.

What is claimed is:

1. A method of initiating a baroreflex response, the method comprising:
   accessing a first blood vessel having a region capable of initiating the baroreflex response;
   creating an opening in a second blood vessel proximate the region and branching from the first blood vessel;
   inserting a transducer operably carried by a distal end of an apparatus into the opening in the second blood vessel;
   positioning an electrode operably carried by the distal end of the apparatus proximate the region of the first blood vessel; and
   operably connecting the transducer and the electrode to a control unit; and
   causing the control unit to selectively generate a therapy signal delivered to the electrode;
   wherein the first blood vessel and the second blood vessel are both arteries.

2. The method of claim 1, wherein creating the opening in the second arterial blood vessel is accomplished by sacrificing the second arterial blood vessel.

3. The method of claim 1, the method is performed on the high-pressure side of the vasculature.

4. The method of claim 3, wherein creating the opening in the second blood vessel branching from the first blood vessel is performed on a superior thyroid artery branching from a carotid sinus.

5. The method of claim 1, wherein positioning the electrode positions the electrode about an exterior portion of the first blood vessel.

6. The method of claim 1, wherein positioning the electrode positions the electrode about a nerve proximate the first blood vessel.

7. A method of initiating a baroreflex response, the method comprising:

providing a control unit and at least one apparatus adapted to be implanted in a patient; and providing instructions for implanting the at least one apparatus including:

accessing a first blood vessel having a region capable of initiating a baroreflex response;

creating an opening in a second blood vessel proximate the region and branching from the first blood vessel;

inserting a transducer operably carried by a distal end of an apparatus into the opening in the second blood vessel;

positioning an electrode operably carried by the distal end of the apparatus proximate the region of the first blood vessel; and operably connecting the transducer and the electrode to a control unit; and causing the control unit to selectively generate a therapy signal delivered to the electrode in response to a sensor signal representative of the physiologic parameter measured by the transducer;

wherein the first blood vessel and the second blood vessel are both arteries.

8. The method of claim 7, wherein creating the opening in the second arterial blood vessel is accomplished by sacrificing the second arterial blood vessel.

9. The method of claim 7, wherein the method is performed on the high-pressure side of the vasculature.

10. The method of claim 9, wherein creating the opening in the second blood vessel branching from the first blood vessel is performed on a superior thyroid artery branching from an external carotid artery.

11. The method of claim 7, wherein positioning the electrode positions the electrode about an exterior portion of the first blood vessel.

12. The method of claim 7, wherein positioning the electrode positions the electrode about a nerve proximate the first blood vessel.

* * * * *